(12) United States Patent
Cai et al.

(10) Patent No.: US 11,198,904 B2
(45) Date of Patent: Dec. 14, 2021

(54) SUBSTRATE FOR MEDICAL TEST, GENE SEQUENCING METHOD AND GENE SEQUENCING CHIP

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Peizhi Cai, Beijing (CN); Fengchun Pang, Beijing (CN); Yue Geng, Beijing (CN); Chuncheng Che, Beijing (CN); Hailin Xue, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 392 days.

(21) Appl. No.: 16/078,112

(22) PCT Filed: Jan. 26, 2018

(86) PCT No.: PCT/CN2018/074237
§ 371 (c)(1),
(2) Date: Aug. 21, 2018

(87) PCT Pub. No.: WO2019/010955
PCT Pub. Date: Jan. 17, 2019

(65) Prior Publication Data
US 2019/0345547 A1    Nov. 14, 2019

(30) Foreign Application Priority Data

Jul. 10, 2017    (CN) .......................... 201710557848.8

(51) Int. Cl.
| | | |
|---|---|---|
| *C12Q 1/6869* | (2018.01) | |
| *B01L 3/00* | (2006.01) | |
| *C12Q 1/6834* | (2018.01) | |

(52) U.S. Cl.
CPC ........ *C12Q 1/6869* (2013.01); *B01L 3/50273* (2013.01); *B01L 3/502715* (2013.01);
(Continued)

(58) Field of Classification Search
None
See application file for complete search history.

(56) References Cited

U.S. PATENT DOCUMENTS 5,888,390 A * 3/1999 Craig ...................... B01L 3/505
                                                        210/198.2
5,997,708 A   12/1999 Craig
(Continued)

FOREIGN PATENT DOCUMENTS

CN    102245305 B    8/2014
CN    106391151 A    2/2017
(Continued)

OTHER PUBLICATIONS

International Search Report and Written Opinion dated Apr. 28, 2018 from State Intellectual Property Office of the P.R. China.
(Continued)

*Primary Examiner* — Lore R Jarrett
(74) *Attorney, Agent, or Firm* — Dilworth & Barrese, LLP.; Michael J. Musella, Esq.

(57) ABSTRACT

A substrate for medical test and a gene sequencing method thereof are disclosed. The substrate for medical test includes a micro flow channel substrate, a first substrate, and a second substrate. A side of the micro flow channel substrate facing the first substrate is provided with at least one first micro flow channel, and the first substrate includes a first sample (Continued)

inlet and a first sample outlet which are in communication with the first micro flow channel; a side of the micro flow channel substrate facing the second substrate is provided with at least one second micro flow channel, and the second substrate includes a second sample inlet and a second sample outlet which are communication with the second micro flow channel.

17 Claims, 4 Drawing Sheets

(52) U.S. Cl.
CPC ........ *C12Q 1/6834* (2013.01); *B01L 2200/10* (2013.01); *B01L 2300/0861* (2013.01)

(56) References Cited

U.S. PATENT DOCUMENTS

| | | | | |
|---|---|---|---|---|
| 6,033,544 A * | 3/2000 | Demers | ............... | B01F 15/0264 |
| | | | | 204/450 |
| 6,485,690 B1 * | 11/2002 | Pfost | ................... | B01J 19/0046 |
| | | | | 422/552 |
| 6,966,212 B2 * | 11/2005 | Klee | ..................... | G01N 30/12 |
| | | | | 73/23.41 |
| 9,101,933 B2 | 8/2015 | Haswell | | |
| 9,630,177 B2 | 4/2017 | Stern et al. | | |
| 10,379,101 B2 | 8/2019 | Yu et al. | | |
| 2005/0037471 A1 * | 2/2005 | Liu | ...................... | F04B 43/043 |
| | | | | 435/91.2 |
| 2009/0191617 A1 | 7/2009 | Lim et al. | | |
| 2010/0075340 A1 | 3/2010 | Javanmard et al. | | |
| 2015/0093303 A1 | 4/2015 | Tsai et al. | | |
| 2018/0187248 A1 | 7/2018 | Pang et al. | | |
| 2018/0237846 A1 | 8/2018 | Geng et al. | | |

FOREIGN PATENT DOCUMENTS

| | | |
|---|---|---|
| CN | 106461697 A | 2/2017 |
| CN | 106591109 A | 4/2017 |
| CN | 106754312 A | 5/2017 |
| CN | 106757376 A | 5/2017 |
| EP | 1418233 A1 | 5/2004 |

OTHER PUBLICATIONS

Extended European Search Report from EPO Patent Application No. 18752078.8 dated Nov. 24, 2020.

Indian Search Report from Indian Patent Application No. 20187030694 dated Nov. 24, 2020.

First Chinese Office Action from Chinese Patent Application No. 201710557848.8 dated Mar. 31, 2021.

* cited by examiner

SUBSTRATE FOR MEDICAL TEST, GENE SEQUENCING METHOD AND GENE SEQUENCING CHIP

CROSS REFERENCE

The present application claims priority of China Patent application No. 201710557848.8 filed on Jul. 10, 2017, the content of which is incorporated in its entirety as portion of the present application by reference herein.

TECHNICAL FIELD

Embodiments of the present disclosure relate to a substrate for medical test, a gene sequencing method of the substrate for medical test, and a gene sequencing chip.

BACKGROUND

With the continuous development of gene sequencing technology, the gene sequencing technology has gradually become the most commonly used technology in the modern molecular biology research, with a wide range of applications. Therefore, a device for gene sequencing has a relatively large market space.

Since the first generation of gene sequencing in 1977, the gene sequencing technology has achieved considerable progress, with the first generation of sanger sequencing technology, the second generation of high throughput sequencing technology, the third generation of single molecule sequencing technology, and the fourth generation of nanopore sequencing technology. The current mainstream sequencing technology is still dominated by the second generation of high throughput sequencing technology.

The second-generation of high throughout sequencing technology mainly includes the technology of sequencing by synthesis of Illumina, an ion semiconductor sequencing technology of Thermo Fisher, a linking sequencing technology and a pyrosequencing technology of Roche and so on.

SUMMARY

Embodiments of the present disclosure provide a substrate for medical test, a gene sequencing method thereof, and a gene sequencing chip.

At least one embodiment of the present disclosure provides a substrate for medical test, including: a micro flow channel substrate; a first substrate, located opposite to the micro flow channel substrate; a second substrate, located opposite to the micro flow channel substrate and on a side of the micro flow channel substrate away from the first substrate, a surface of the micro flow channel substrate facing the first substrate is provided with at least one first micro flow channel, and the first substrate includes a first sample inlet and a first sample outlet which are in communication with the first micro flow channel, a surface of the micro flow channel substrate facing the second substrate is provided with at least one second micro flow channel, and the second substrate includes a second sample inlet and a second sample outlet which are communication with the second micro flow channel.

For example, in the substrate for medical test provided by an embodiment of the present disclosure, an orthographic projection of the first micro flow channel on the micro flow channel substrate and an orthographic projection of the second micro flow channel on the micro flow channel substrate are at least partially overlapped with each other.

For example, in the substrate for medical test provided by an embodiment of the present disclosure, an orthographic projection of the first micro flow channel on the micro flow channel substrate and an orthographic projection of the second micro flow channel on the micro flow channel substrate are not overlapped with each other.

For example, in the substrate for medical test provided by an embodiment of the present disclosure, the first sample inlet and the first sample outlet are located at two ends of the corresponding first micro flow channel respectively, the second sample inlet and the second sample outlet are located at two ends of the corresponding second micro flow channel respectively.

For example, in the substrate for medical test provided by an embodiment of the present disclosure, the first substrate includes a plurality of first sequencing wells recessed into the first substrate from a side of the first substrate close to the micro flow channel substrate, each of the first sequencing wells is in communication with the corresponding first micro flow channel and disposed between the corresponding first sample inlet and the corresponding first sample outlet, and each of the first sequencing wells is configured to place a sample to be tested.

For example, in the substrate for medical test provided by an embodiment of the present disclosure, the second substrate includes a plurality of second sequencing wells recessed into the second substrate from a side of the second substrate close to the micro flow channel substrate, each of the second sequencing wells is in communication with the corresponding second micro flow channel and disposed between the corresponding second sample inlet and the corresponding second sample outlet, and each of the second sequencing wells is configured to place a sample to be tested.

For example, in the substrate for medical test provided by an embodiment of the present disclosure, a depth of the first micro flow channel and/or the second micro flow channel are/is in a range of 10-500 μm.

For example, in the substrate for medical test provided by an embodiment of the present disclosure, a width of the first micro flow channel and/or the second micro flow channel are/is in a range of 100-10000 μm.

For example, in the substrate for medical test provided by an embodiment of the present disclosure, a material of the first substrate and/or the second substrate includes quartz, glass or an organic resin.

At least one embodiment of the present disclosure provides a gene sequencing chip, including the substrate for medical test according to any one of the abovementioned examples.

For example, in the gene sequencing chip provided by an embodiment of the present disclosure, the first micro flow channel includes a plurality of first sequencing regions which are spaced apart from each other, and each of the first sequencing regions is configured to place a sample to be tested.

For example, in the gene sequencing chip provided by an embodiment of the present disclosure, the first sequencing regions are sequentially disposed along an extending direction of the first micro flow channel.

For example, in the gene sequencing chip provided by an embodiment of the present disclosure, the second micro flow channel includes a plurality of second sequencing regions which are spaced apart, and each of the second sequencing regions is configured to place a sample to be tested.

For example, in the gene sequencing chip provided by an embodiment of the present disclosure, the second sequencing regions are sequentially disposed along an extending direction of the second micro flow channel.

At least one embodiment of the present disclosure provides a gene sequencing method for a substrate for medical test, wherein the substrate for medical test includes the substrate for medical test according to any one of the abovementioned examples, and the gene sequencing method includes: through the first sample inlet, sequentially introducing four different deoxyribonucleoside triphosphates into the first micro flow channel in communication with the first sample inlet; and through the second sample inlet, sequentially introducing four different deoxyribonucleoside triphosphates into the second micro flow channel in communication with the second sample inlet.

BRIEF DESCRIPTION OF THE DRAWINGS

In order to clearly illustrate the technical solution of embodiments of the present disclosure, the drawings of the embodiments will be briefly described in the following, it is obvious that the drawings in the description are only related to some embodiments of the present disclosure and not limited to the present disclosure.

DETAILED DESCRIPTION

In order to make objects, technical details and advantages of the embodiments of the present disclosure apparently, the technical solutions of the embodiments will be described in a clearly and fully understandable way in communication with the drawings related to the embodiments of the present disclosure. It is obvious that the described embodiments are just a part but not all of the embodiments of the present disclosure. Based on the described embodiments herein, a person having ordinary skill in the art may obtain other embodiment(s), without any inventive work, which should be within the scope of the disclosure.

Unless otherwise defined, the technical terms or scientific terms utilized herein have the same meanings as commonly understood by one of ordinary skill in the art to which the present disclosure belongs. The terms "first", "second", etc., which are utilized in the description and the claims of the present disclosure, are not intended to characterize any sequence, amount or importance, but distinguish various components. The terms "includes", "including", etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly.

At present, the mainstream second generation of substrate for medical test on the market is a flow-cell sequencing chip, which accounts for more than 90% of the market. However, the usual flow-cell sequencing chip has relatively high manufacturing costs, and the usual sequencing chip is mainly formed by a two-layer structure to form a single-layer micro flow channel, such that the sequencing ability is limited, resulting in low efficiency and high cost of gene sequencing.

Figure 1:
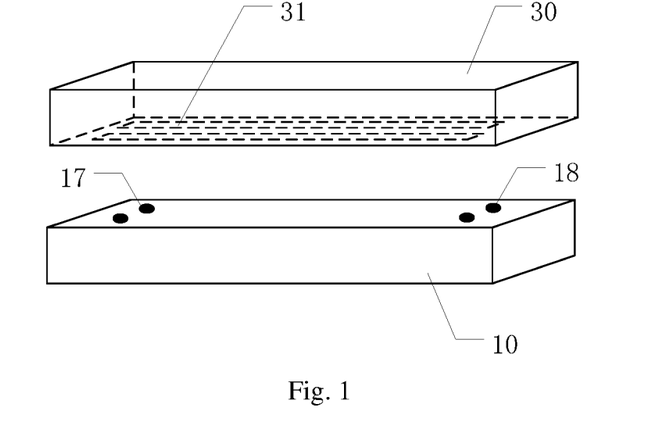
FIG. 1 is a schematic structural diagram of a substrate for medical test.
Figure 2:
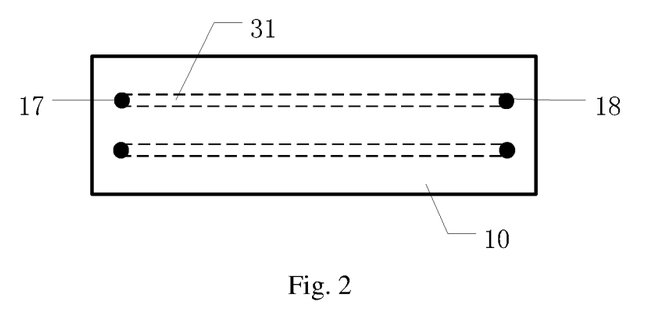
FIG. 2 is a schematic plan view of a substrate for medical test.
Figure 3:
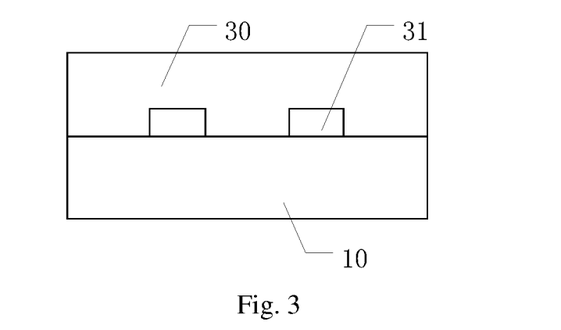
FIG. 3 is schematic side view of a substrate for medical test.

For example, FIG. 1 is a schematic diagram of a substrate for medical test. As illustrated by FIG. 1, the substrate for medical test includes a substrate 10 and a micro flow channel substrate 30 which are disposed opposite each other. A surface of the micro flow channel substrate 30 close to the substrate 10 is provided with at least one micro flow channel 31, and FIG. 1 shows two micro flow channels. The substrate 10 is provided with at least one pair of sample inlet 17 and sample outlet 18 corresponding to the at least one micro flow channel 31, and the sample inlet 17 and sample outlet 18 are in communication with the corresponding micro flow channel 31. In FIG. 1, in order to clearly show the structure of the substrate 10 and the micro flow channel substrate 30, the substrate 10 and the micro flow channel substrate 30 are spaced apart by a certain distance. However, when used, the substrate 10 and the micro flow channel substrate 30 are in contact with each other. FIG. 2 is a schematic plan view of the substrate for medical test shown in FIG. 1. As illustrated by FIG. 2, two micro flow channels 31 are disposed on the micro flow channel substrate 30, and two pairs of sample inlet 17 and sample outlet 18 corresponding to the two micro flow channels 31 are disposed on the substrate 10. FIG. 3 is a schematic side view of the substrate for medical test shown in FIG. 1. As illustrated by FIG. 3, the micro flow channel 31 is a groove structure which is recessed into the micro flow channel substrate 30 from the surface of the micro flow channel substrate 30 close to the substrate 10. Because the substrate for medical test shown in FIGS. 1 to 3 forms the micro flow channel 31 and the correspondingly disposed sample inlet 17 and the sample outlet 18 through the substrate 10 and the micro flow channel substrate 40, the sequencing ability is limited, resulting in low efficiency and high cost of gene sequencing.

Embodiments of the present disclosure provide a substrate for medical test, a gene sequencing method thereof, and a gene sequencing chip. The substrate for medical test includes a micro flow channel substrate, a first substrate located opposite to the micro flow channel substrate, and a second substrate located opposite to the micro flow channel substrate and disposed on a side of the micro flow channel substrate away from the first substrate. A side of the micro flow channel substrate facing the first substrate is provided with at least one first micro flow channel, the first substrate includes a first sample inlet and a first sample outlet in communication with the first micro flow channel; a side of the micro flow channel substrate facing the second substrate is provided with at least one second micro flow channel, the second substrate includes a second sample inlet and a second sample outlet in communication with the second micro flow channel Thus, by providing the first substrate and the second substrate on two sides of the micro flow channel substrate, the micro flow channel substrate is fully utilized, and the first micro flow channel and the second micro flow channel are respectively formed on two sides of the micro flow channel substrate. Thereby, the sequencing ability of the substrate for medical test is doubled. When used for gene detection, the sequencing throughput and the efficiency of gene sequencing can be improved, and the cost of gene sequencing can be reduced. In addition, the substrate for medical test also reduces the time for frequent replacement of the substrate for medical test and loading of chemical reagents, thereby further improving the efficiency of gene sequencing.

Hereinafter, the substrate for medical test, the gene sequencing method thereof, and the gene detection substrate provided by the embodiments of the present disclosure will be described with reference to the accompanying drawings.

At least one embodiment of the present disclosure provides a substrate for medical test. The substrate for medical test includes a micro flow channel substrate, a first substrate located opposite to the micro flow channel substrate, and a second substrate located opposite to the micro flow channel substrate and disposed on a side of the micro flow channel substrate away from the first substrate. A side of the micro flow channel substrate facing the first substrate is provided with at least one first micro flow channel, the first substrate includes a first sample inlet and a first sample outlet in communication with the first micro flow channel; a side of the micro flow channel substrate facing the second substrate is provided with at least one second micro flow channel, the second substrate includes a second sample inlet and a second sample outlet in communication with the second micro flow channel.

Figure 4:
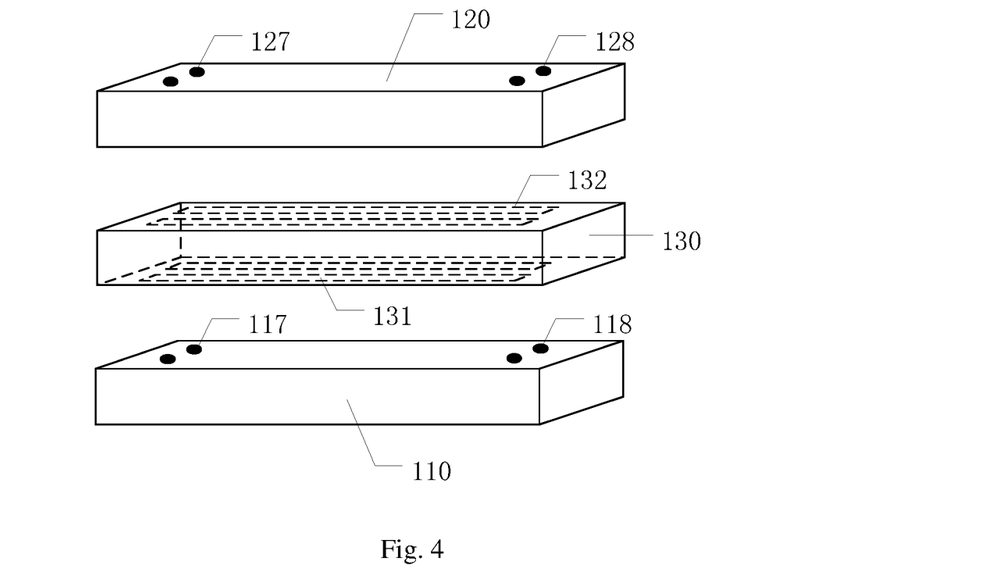
FIG. 4 is a schematic structural diagram of a substrate for medical test provided by an embodiment of the present disclosure.

FIG. 4 is a schematic structural diagram of a substrate for medical test according to an embodiment of the present disclosure. As illustrated by FIG. 1, the substrate for medical test includes a first substrate 110, a second substrate 120, and a micro flow channel substrate 130. The first substrate 110 is located opposite to the micro flow channel substrate 130, and the second substrate 120 is located opposite to the micro flow channel substrate 130 and disposed on a side of the micro flow channel substrate 130 away from the first substrate 110; that is, the first substrate 110 and the second substrate 120 are disposed to opposite to two side surfaces of the micro flow channel substrate 130 respectively. A surface of the micro flow channel substrate 130 opposite to the first substrate 110 (i.e., the surface of the micro flow channel substrate 130 facing the first substrate 110) is provided with at least one first micro flow channel 131, and the first substrate 110 includes a first sample inlet 117 and a first sample outlet 118 which are in communication with the first micro flow channel 131. A surface of the micro flow channel substrate 130 opposite to the second substrate 120 (i.e., the surface of the micro flow channel substrate 130 facing the second substrate 120) is provided with at least one second micro flow channel 132, and the second substrate 120 includes the a second sample inlet 127 and a second sample outlet 128 which are in communication with second micro flow channel 132. It should be noted that the first micro flow channel can be provided in plural, and the second micro flow channel can be provided in plural; in a case where the micro flow channel substrate includes a plurality of first micro flow channels, the first substrate also includes a plurality of pairs of the first sample inlet and the first sample outlet, and each of the first micro flow channels corresponds to one pair of first sample inlet and the first sample outlet; and in a case where the micro flow channel substrate includes a plurality of second micro flow channels, the second substrate also includes a plurality of pairs of the second sample inlet and the second sample outlet, and each of the second micro flow channels corresponds to one pair of second sample inlet and the second sample outlet.

In the substrate for medical test provided by the present embodiment, various chemical reagents can be introduced into or discharged from the first micro flow channel through the first sample inlet and the first sample outlet; for example, the chemical reagents include four types of deoxyribonucleoside triphosphate solutions different in base. Various chemical reagents can be introduced into or discharged from the second micro flow channel through the second sample inlet and the second sample outlet; for example, the chemical reagents include four types of deoxyribonucleoside triphosphate solutions different in basic group, so as to simultaneously complete gene sequencing in the first micro flow channel and the second micro flow channel which are located at two sides of the micro flow channel substrate. The substrate for medical test can fully utilize the micro flow channel substrate, by forming the first micro flow channel and the second micro flow channel on two sides of the micro flow channel substrate respectively, such that the detection ability of the substrate for medical test can be doubled. When used for gene sequencing, the gene sequencing ability of the substrate for medical test is doubled, so that the sequencing throughput and gene sequencing efficiency can be improved, and the costs of gene sequencing can be reduced. In addition, due to the increase of the sample to be tested that can be accommodated by the substrate for medical test at one time, the substrate for medical test also reduces the time for frequent replacement of the substrate for medical test and loading of chemical reagents, thereby further improving the efficiency of gene sequencing. It should be noted that the substrate for medical test provided by the embodiments of the present disclosure can also be applied to other medical test applications.

It is to be noted that, in FIG. 4, in order to clearly show the structures of the first substrate 110, the second substrate 120, and the micro flow channel substrate 130, the first substrate 110 and the micro flow channel substrate 130 are spaced apart by a certain distance, and the second substrate 120 and the micro flow channel substrate 130 are spaced apart by a certain distance. However, in actual use, the first substrate 110 and the micro flow channel substrate 130 are in contact with each other, and the second substrate 120 and the micro flow channel substrate 130 are in contact with each other.

For example, the first micro flow channel 131 is a groove structure which is recessed into the micro flow channel substrate 130 from the surface of micro flow channel substrate 130 close to the first substrate 110; and the second micro flow channel 132 is a groove structure which is recessed into the micro flow channel substrate 130 from the surface of micro flow channel substrate 130 close to the second substrate 120.

Figure 5:
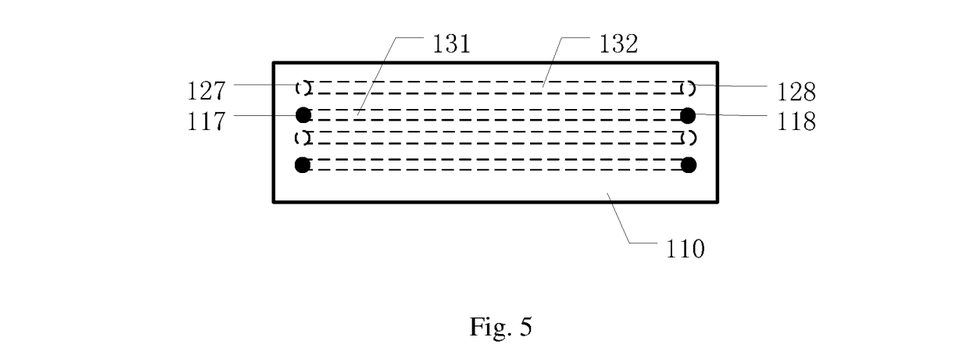
FIG. 5 is a schematic plan diagram of a substrate for medical test provided by an embodiment of the present disclosure.

FIG. 5 is a schematic plan view of the substrate for medical test shown in FIG. 4. As illustrated by FIG. 5, the first sample inlet 117 and the first sample outlet 118 are respectively disposed at two ends of the corresponding first micro flow channel 131, and the second sample inlet 127 and the second sample outlet 128 are respectively disposed at two ends of a corresponding second micro flow channel 132. Thereby, various chemical reagents can be introduced into or discharged from the first micro flow channel through the first sample inlet and the first sample outlet, and various chemical reagents can be introduced to or discharged from the second micro flow channel through the second sample inlet and the second sample outlet, the efficiency can be increased and the reagent residues can be avoided.

Figure 6:
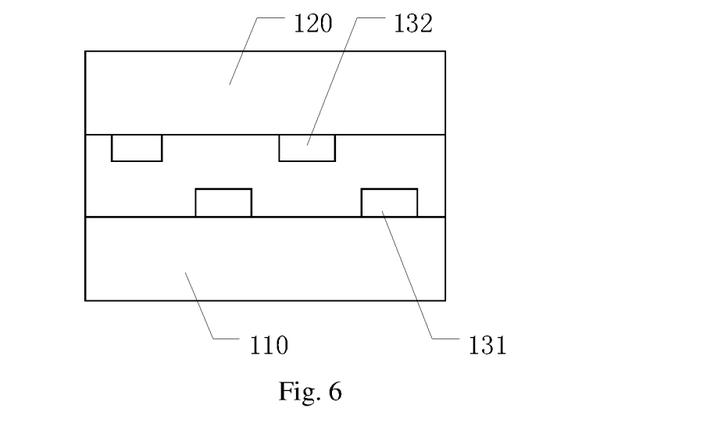
FIG. 6 is a schematic side diagram of a substrate for medical test provided by an embodiment of the present disclosure.

FIG. 6 is a schematic side view of the substrate for medical test shown in FIG. 4. As illustrated by FIG. 6, an orthographic projection of the first micro flow channel 131 on the micro flow channel substrate 130 and an orthographic projection of the second micro flow channel 132 on the micro flow channel substrate 130 are not overlapped with each other. Thereby, interference between the first micro flow channel and the second micro flow channel which are adjacent to each other can be reduced. Of course, embodiments of the present disclosure include but are not limited thereto.

Figure 7:
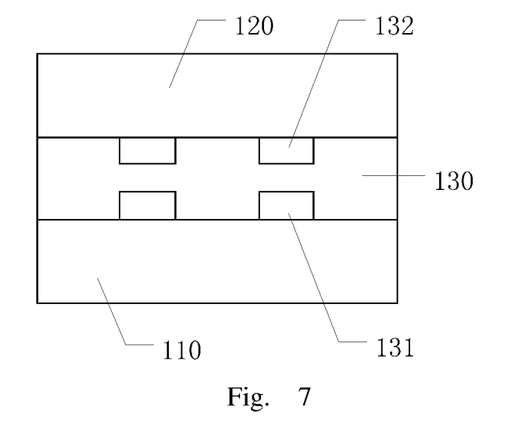
FIG. 7 is a schematic side diagram of another substrate for medical test provided by an embodiment of the present disclosure.

For example, FIG. 7 is a schematic side view of another substrate for medical test according to the present embodiment. As illustrated by FIG. 7, the orthographic projection of the first micro flow channel 131 on the micro flow channel substrate 130 and the orthographic projection of the second micro flow channel 132 on the micro flow channel substrate 130 are at least partially overlapped or even completely overlapped with each other. An interval between adjacent first micro flow channels and an interval between adjacent second micro flow channels can be reduced to increase the number of the first micro flow channels and the second micro flow channels on the substrate for medical test.

In some examples, the number of first micro flow channels ranges from 1-10. Of course, embodiments of the present disclosure include, but are not limited thereto, and the number of the first micro flow channels can be greater than 10.

In some examples, the number of second micro flow channels ranges from 1-10. Of course, embodiments of the present disclosure include but are not limited thereto, and the number of the second micro flow channels can be greater than 10.

In some examples, a depth of the first micro flow channel can range from 10 to 500 μm, and a depth of the second micro flow channel can range from 10 to 500 μm. Of course, embodiments of the present disclosure include but are not limited thereto.

In some examples, a width of the first micro flow channel ranges from 100 to 10,000 μm, and a width of the second micro flow channel ranges from 100 to 10,000 μm. Of course, embodiments of the present disclosure include but are not limited thereto.

In some examples, a material of the first substrate includes quartz, glass, or an organic resin, and a material of the second substrate includes quartz, glass, or an organic resin.

Figure 8:
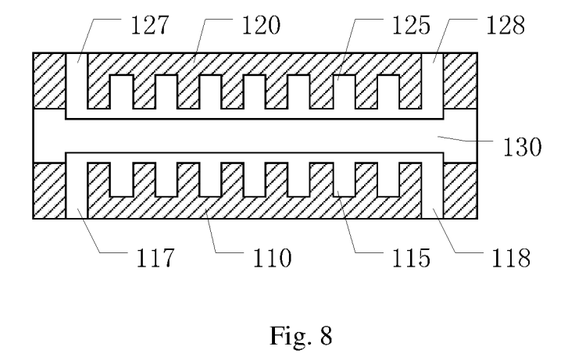
FIG. 8 is a schematic side diagram of a gene sequencing chip provided by an embodiment of the present disclosure.

FIG. 8 is a schematic sectional view of another gene sequencing chip according to the present embodiment. As illustrated by FIG. 8, the first substrate 110 includes a plurality of first sequencing wells 115 recessed from a side of the first substrate 110 close to the micro flow channel substrate 130, and each of the first sequencing wells 115 is in communication with a corresponding first micro flow channel 131 and is disposed between a corresponding first sample inlet 117 and a corresponding first sample outlet 118; and each of the first sequencing wells 115 can be configured to place a sample to be tested. Thereby, various chemical reagents can be applied to the first micro flow channel 131 through the first sample inlet 117, for example, the various chemical reagents include four types of deoxyribonucleoside triphosphate solutions different in base, and then various chemical reagents are introduced into each of first sequencing wells 115 with the sample to be tested therein to react with the sample to be tested, and then discharged through the first sample port 118, thereby completing gene sequencing of the sample to be tested.

In some examples, as illustrated by FIG. 8, the second substrate 120 includes a plurality of second sequencing wells 125 recessed into the second substrate 120 from a side of the second substrate 120 close to the micro flow channel substrate 130; each of the second sequencing wells 125 is in communication with a corresponding second micro flow channel 132 and disposed between a corresponding second sample inlet 127 and a corresponding second sample outlet 128. Each of the second sequencing wells 125 can be configured to place a sample to be tested. Thereby, various chemical reagents can be applied to the second micro flow channel 132 through the second sample inlet 127, for example, the various chemical reagents include four types of deoxyribonucleoside triphosphate solutions different in base, and then the various chemical reagents can be introduced into each of the second sequencing wells 125 with the sample to be tested therein to react with the sample to be tested, and then discharged from the second sample outlet 128, so as to complete the gene sequencing of the sample to be tested.

For example, a cross-sectional shape of the first sequencing well or the second sequencing well can be a shape of a circle, a regular polygon, or the like.

Figure 9A:
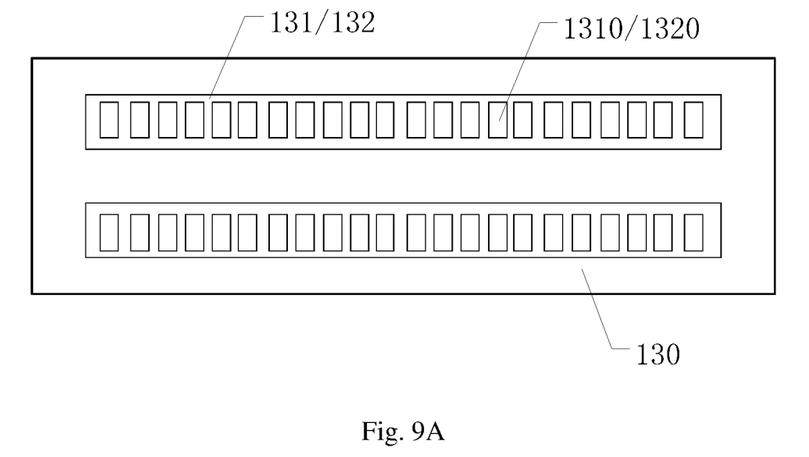
FIG. 9A is a schematic plan view of a micro flow channel substrate provided by an embodiment of the present disclosure.

It should be noted that the gene sequencing chip provided by the embodiments of the present disclosure can be not provided with the first sequencing well on the first substrate, and the second sequencing well on the second substrate. FIG. 9A shows a schematic plan view of a micro flow channel substrate according to the present embodiment. As illustrated by FIG. 9A, the first micro flow channel 131 includes a plurality of first sequencing regions 1310 which are spaced apart from each other, and each of the first sequencing regions 1310 can be used to accommodate a sample to be tested. Thus, various chemical reagents can be applied to the first micro flow channel 131; for example, the various chemical reagents include four types of deoxyribonucleoside triphosphate solutions different in base. Therefore, it is possible for the various chemical reagents to directly react with different samples to be tested in different first sequencing regions 1310, so as to complete gene sequencing of the sample to be tested. For example, as illustrated by FIG. 9A, the second micro flow channel 132 includes a plurality of second sequencing regions 1320 which are spaced apart, and each of the second sequencing regions 1320 can be used to place a sample to be tested. Thus, various chemical reagents can be applied to the second micro flow channel 132; for example, the various chemical reagents includes four types of deoxyribonucleoside triphosphate solutions different in base. Therefore, it is possible for the various chemical reagents to react with different samples to be tested in different second sequencing regions 1320, so as to complete gene sequencing of the sample to be tested.

Figure 9B:
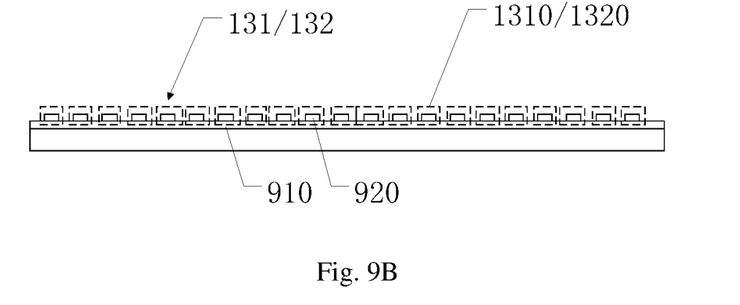
FIG. 9B is a schematic cross sectional view of a micro flow channel substrate provided by an embodiment of the present disclosure.

It should be noted that the sample to be tested can be limited in the first sequencing region or the second sequencing region, so as to prevent the sample to be tested from flowing into the first micro flow channel or the second micro flow channel. For example, as illustrated by FIG. 9B, a gel layer 910 can be formed in the first sequencing region 1310 or the second sequencing region 1320, and a joint 920 can be disposed on the gel layer 910. The sample to be tested can be fixed in the first sequencing region or the second sequencing region by attaching the sample to be tested to the joint 920 on the gel layer 910 through a pairing manner. The gel layer can be made of a conventional material, for example, a hydrogel. Furthermore, for example, the gel layer can be made of a substance having a gel-like structure, a substance having a polymer network structure, or a substance having a cross-linked polymer structure. For example, the substance having a gel-like structure includes agarose, the substance having a polymer network structure includes gelatin, and the substance having a cross-linked polymer structure includes polyacrylamide. The gel layer material can also be silane-free acrylamide or N-[5-(2-bromoacetyl)aminopentyl]acrylamide (BRAPA).

For example, as illustrated by FIG. 9A, the plurality of first sequencing regions 1310 can be sequentially disposed along an extending direction of the first micro flow channel 131.

For example, as illustrated by FIG. 9A, the plurality of second sequencing regions 1320 can be sequentially disposed along an extending direction of the second micro flow channel 132.

Figure 10:
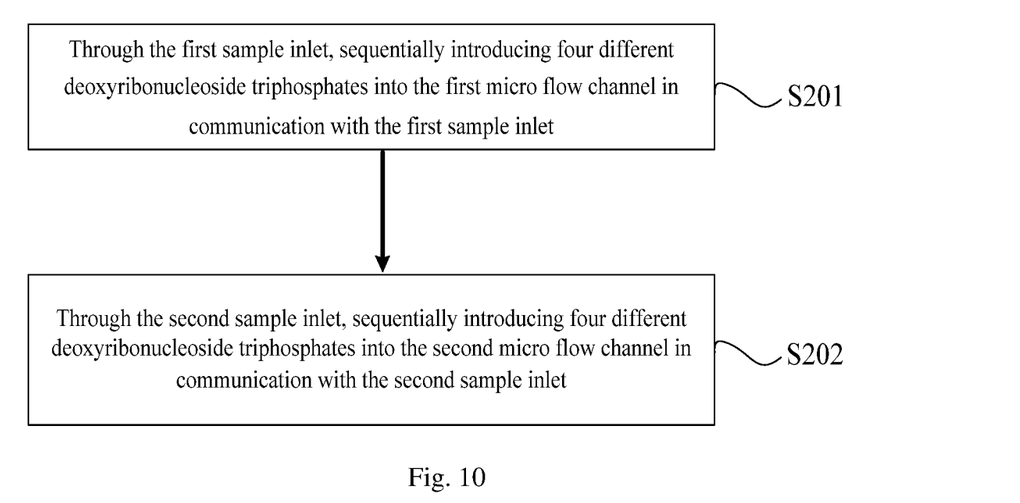
FIG. 10 is a flow diagram of a gene sequencing method of a micro flow channel substrate provided by an embodiment of the present disclosure.

At least one embodiment of the present disclosure also provides a gene sequencing method for a substrate for medical test. The substrate for medical test can employ the substrate for medical test described in any one of the abovementioned examples. FIG. 10 is a flow diagram of a gene sequencing method of a substrate for medical test. The gene sequencing method includes the following steps S201-S202.

Step S201: through the first sample inlet, sequentially introducing four different deoxyribonucleoside triphosphates into the first micro flow channel in communication with the first sample inlet.

Step S202: through the second sample inlet, sequentially introducing four different deoxyribonucleoside triphosphates into the second micro flow channel in communication with the second sample inlet.

It should be noted that the abovementioned steps S201 and S202 do not have a chronological order, namely, step S201 and step S202 can be performed simultaneously.

In the gene sequencing method of the substrate for medical test provided by the present embodiment, various chemical reagents can be introduced into or discharged from the first micro flow channel through the first sample inlet and the first sample outlet, for example, the various chemical reagents include four types of deoxyribonucleoside triphosphate solutions different in base; and various chemical reagents can be introduced into or discharged from the second micro flow channel through the second sample inlet and the second sample outlet, for example, the various chemical reagents including four types of deoxyribonucleoside triphosphate solutions different in base, so as to simultaneously complete gene sequencing in the first micro flow channel and the second micro flow channel which are located on two sides of the micro flow channel substrate. The gene sequencing method can fully utilize the first micro flow channel and the second micro flow channel located on two sides of the micro flow channel substrate, so as to double the gene sequencing ability, improve the sequencing throughput and gene sequencing efficiency, and reduce the costs of gene sequencing.

For example, the abovementioned deoxyribonucleoside triphosphate includes a reversible terminating deoxyribonucleoside triphosphate, the gene sequencing method further includes: cleaning the reversible terminating deoxyribonucleoside triphosphate introduced in the sequencing wells, and adding a mercapto reagent. After completing a basic group type detection for a previous position of the sample to be tested (for example, a DNA fragment), the reversible terminating deoxyribonucleoside triphosphate introduced in the sequencing wells needs to be cleaned, and then the mercapto reagent is added. It should be noted that: unlike an ordinary deoxyribonucleoside triphosphate, a 3'-end of the reversible terminating deoxyribonucleoside triphosphate is linked with an azide group, which does not form a phosphodiester bond during a DNA synthesis process, and thus the DNA synthesis process can be interrupted. If the mercapto reagent is added, the azide group will break, and a hydroxyl group can be formed at an original position. A base type detection of a subsequent location of the sample to be tested can be performed after adding the mercapto reagent, the detection method is the same as the abovementioned method, which is not repeated herein.

For example, in a case that the sample to be tested is a DNA fragment, the abovementioned reversible terminating deoxyribonucleoside triphosphate can include a reversible terminating deoxy adenine triphosphate, a reversible terminating deoxy thymine triphosphate, a reversible terminating deoxy cytosine triphosphate, and a reversible terminating deoxy guanine triphosphate. If the deoxyribonucleoside triphosphate introduced and reacted in the sequencing wells is the adenine deoxyribonucleoside triphosphate, and then the base in the sample to be tested (for example, the DNA fragment) is a thymine; if the deoxyribonucleoside triphosphate introduced and reacted in the sequencing wells is the thymidine deoxyribonucleoside triphosphate, and then the base in the sample to be tested (for example, the DNA fragment) is an adenine; if the deoxyribonucleoside triphosphate introduced and reacted in the sequencing wells is the cytosine deoxyribonucleoside triphosphate, and then the base in the sample to be tested (for example, the DNA fragment) is a guanine; if the deoxyribonucleoside triphosphate introduced and reacted in the sequencing wells is the guanine deoxyribonucleotide triphosphate, and then the base in the sample to be tested (for example, the DNA fragment) is a cytosine.

The following points should to be explained:

(1) The drawings of the embodiments of the present disclosure only relate to the structure related to the embodiments of the present disclosure, and other structures can be referenced to the usual design.

(2) In the absence of conflict, the features of the same embodiment and the different embodiments can be combined with each other.

The foregoing is only the embodiments of the present disclosure and not intended to limit the scope of protection of the present disclosure, alternations or replacements which can be easily envisaged by any skilled person being familiar with the present technical field shall fall into the protection scope of the present disclosure. Thus, the protection scope of the present disclosure should be based on the protection scope of the claims.

What is claimed is:

1. A substrate for medical test, comprising:
   a micro flow channel substrate;
   a first substrate, located opposite to the micro flow channel substrate;
   a second substrate, located opposite to the micro flow channel substrate and on a side of the micro flow channel substrate away from the first substrate, wherein a surface of the micro flow channel substrate facing the first substrate is provided with a first micro flow channel, and the first substrate comprises a first sample inlet and a first sample outlet which are in communication with the first micro flow channel, a surface of the micro flow channel substrate facing the second substrate is provided with a second micro flow channel, and the second substrate comprises a second sample inlet and a second sample outlet which are in communication with the second micro flow channel the first micro flow channel is a first groove structure which is recessed into the micro flow channel substrate from the surface of the micro flow channel substrate facing the first substrate, and the second micro flow channel is a second groove structure which is recessed into the micro flow channel substrate from the surface of the micro flow channel substrate facing the second substrate;

a depth of the first groove structure and a depth of the second groove structure both are smaller than a depth of the micro flow channel substrate, and the first micro flow channel and the second micro flow channel are fluidly isolated from each other.

2. The substrate for medical test according to claim 1, wherein an orthographic projection of the first micro flow channel on the micro flow channel substrate and an orthographic projection of the second micro flow channel on the micro flow channel substrate are at least partially overlapped with each other.

3. The substrate for medical test according to claim 1, wherein an orthographic projection of the first micro flow channel on the micro flow channel substrate and an orthographic projection of the second micro flow channel on the micro flow channel substrate are not overlapped with each other.

4. The substrate for medical test according to claim 1, wherein the first sample inlet and the first sample outlet are located at two ends of the corresponding first micro flow channel respectively, the second sample inlet and the second sample outlet are located at two ends of the corresponding second micro flow channel respectively.

5. The substrate for medical test according to claim 4, wherein the first substrate comprises a plurality of first sequencing wells recessed into the first substrate from a side of the first substrate close to the micro flow channel substrate, each of the first sequencing wells is in communication with the corresponding first micro flow channel and disposed between the corresponding first sample inlet and the corresponding first sample outlet, and each of the first sequencing wells is configured to place a sample to be tested, a depth of each first sequencing well is smaller than a depth of the first substrate, and with the first micro flow channel and the second micro flow channel being fluidly isolated from each other.

6. The substrate for medical test according to claim 4, wherein the second substrate comprises a plurality of second sequencing wells recessed into the second substrate from a side of the second substrate close to the micro flow channel substrate, each of the second sequencing wells is in communication with the corresponding second micro flow channel and disposed between the corresponding second sample inlet and the corresponding second sample outlet, and each of the second sequencing wells is configured to place a sample to be tested, a depth of each second sequencing well is smaller than a depth of the second substrate, and with the first micro flow channel and the second micro flow channel being fluidly isolated from each other.

7. The substrate for medical test according to claim 1, wherein a depth of the first micro flow channel and/or the second micro flow channel are/is in a range of 10-500 μm.

8. The substrate for medical test according to claim 1, wherein a width of the first micro flow channel and/or the second micro flow channel are/is in a range of 100-10000 μm.

9. The substrate for medical test according to claim 1, wherein a material of the first substrate and/or the second substrate comprises quartz, glass or an organic resin.

10. A gene sequencing chip, comprising the substrate for medical test according to claim 1.

11. The gene sequencing chip according to claim 10, wherein the first micro flow channel comprises a plurality of first sequencing regions which are spaced apart from each other, and each of the first sequencing regions is configured to place a sample to be tested.

12. The gene sequencing chip according to claim 10, further comprising:
   a gel layer, located in each of the first sequencing regions; and
   a joint, located on the gel layer and configured to attach the sample to be tested.

13. The gene sequencing chip according to claim 12, wherein the first sequencing regions are sequentially disposed along an extending direction of the first micro flow channel.

14. The gene sequencing chip according to claim 10, wherein the second micro flow channel comprises a plurality of second sequencing regions which are spaced apart, and each of the second sequencing regions is configured to place a sample to be tested.

15. The gene sequencing chip according to claim 14, further comprising:
   a gel layer, located in each of the second sequencing regions; and
   a joint, located on the gel layer and configured to attach the sample to be tested.

16. The gene sequencing chip according to claim 15, wherein the second sequencing regions are sequentially disposed along an extending direction of the second micro flow channel.

17. A gene sequencing method of a substrate for medical test, wherein the substrate for medical test comprises the substrate for medical test according to claim 1, and the gene sequencing method comprises:
   through the first sample inlet, sequentially introducing four different deoxyribonucleoside triphosphates into the first micro flow channel in communication with the first sample inlet; and
   through the second sample inlet, sequentially introducing four different deoxyribonucleoside triphosphates into the second micro flow channel in communication with the second sample inlet.

\* \* \* \* \*